(12) United States Patent
Sukovic et al.

(10) Patent No.: US 7,611,281 B2
(45) Date of Patent: Nov. 3, 2009

(54) RECONFIGURABLE COMPUTER TOMOGRAPHY SCANNER

(75) Inventors: Predrag Sukovic, Birmingham, MI (US); Miodrag Rakic, Redondo Beach, CA (US)

(73) Assignee: Xoran Technologies, Inc., Ann Arbor, MI (US)

( * ) Notice: Subject to any disclaimer, the term of this patent is extended or adjusted under 35 U.S.C. 154(b) by 0 days.

(21) Appl. No.: 11/032,503

(22) Filed: Jan. 10, 2005

(65) Prior Publication Data

US 2005/0152501 A1    Jul. 14, 2005

Related U.S. Application Data

(60) Provisional application No. 60/535,177, filed on Jan. 8, 2004.

(51) Int. Cl.
*H05G 1/02* (2006.01)

(52) U.S. Cl. ..................................... 378/197

(58) Field of Classification Search ............... 378/198, 378/197, 196
See application file for complete search history.

(56) References Cited

U.S. PATENT DOCUMENTS

| 4,024,401 | A | * | 5/1977 | Bernstein et al. | 378/197 |
| 4,696,025 | A | * | 9/1987 | Taylor | 378/146 |
| 4,979,202 | A | * | 12/1990 | Siczek et al. | 378/198 |
| 5,226,069 | A | * | 7/1993 | Narita | 378/197 |
| 5,500,884 | A | * | 3/1996 | Guenther et al. | 378/38 |
| 5,511,106 | A | * | 4/1996 | Doebert et al. | 378/39 |
| 5,717,735 | A | * | 2/1998 | Ramsdell et al. | 378/208 |
| 5,784,428 | A | * | 7/1998 | Schmidt | 378/4 |
| 6,092,928 | A | * | 7/2000 | Mattson et al. | 378/197 |
| 6,289,074 | B1 | * | 9/2001 | Arai et al. | 378/4 |
| 2002/0085681 | A1 | * | 7/2002 | Jensen | 378/197 |
| 2002/0118793 | A1 | * | 8/2002 | Horbaschek | 378/197 |
| 2003/0235266 | A1 | | 12/2003 | Gregerson et al. | |
| 2004/0013225 | A1 | | 1/2004 | Gregerson et al. | |
| 2004/0013239 | A1 | | 1/2004 | Gregerson et al. | |
| 2004/0022350 | A1 | | 2/2004 | Gregerson et al. | |
| 2004/0170254 | A1 | * | 9/2004 | Gregerson et al. | 378/197 |

* cited by examiner

*Primary Examiner*—Chih-Cheng G Kao
(74) *Attorney, Agent, or Firm*—Carlson, Gaskey & Olds

(57) ABSTRACT

A CT scanner is reconfigurable to multiple orientations and positions. The scanner includes a gantry on which the x-ray source and x-ray detector are mounted. The gantry is mounted on a support and is rotatable about a scan axis relative to the support. The support is movable and/or pivotable relative to a frame, such that the scan axis can be vertical or horizontal.

13 Claims, 5 Drawing Sheets

RECONFIGURABLE COMPUTER TOMOGRAPHY SCANNER

This application claims priority to U.S. Provisional Application Ser. No. 60/535,177, filed Jan. 8, 2004.

BACKGROUND OF THE INVENTION

The present invention relates generally to computer tomography (CT) scanners and more particularly to a compact, reconfigurable CT scanner. Generally, computer tomography scanners are large enough to scan a patient's entire body. Typically, an x-ray source is mounted on a movable ring, which also includes an array of x-ray detectors opposite the x-ray source. The patient lies on a platform that moves through the ring. The ring is rotated so the x-ray source and detectors revolve around the patient, while the patient is moved through the ring on the platform. The x-ray slices through the body by taking a series of x-rays in a spiral pattern. The x-ray source is typically a "fan beam" x-ray source, i.e., it sends a fan-shaped beam that defines a single plane through the body and is received by the detectors.

These scanners are very large because they are capable of scanning an entire body and must include a platform movable through the x-ray source and detectors. An entire room is often dedicated to such a scanner and its associated equipment. Thus, the large scanners are not particularly suited for scanning part of a body, such as the patient's head or extremities.

One known CT scanner, developed by the inventors of the present invention, is disclosed in published U.S. Patent Application No. 2003/0235265. A gantry is rotatably mounted about a vertical axis. An x-ray source and x-ray detector are mounted opposite on another on arms of the gantry. The small CT scanner is particularly adapted to scan a patient's head.

SUMMARY OF THE INVENTION

The present invention provides a CT scanner that is reconfigurable to multiple orientations and positions. The scanner includes a gantry on which the x-ray source and x-ray detector are mounted. The gantry is mounted on a support and is rotatable about a scan axis relative to the support. The support is movable and/or pivotable relative to a frame, such that the scan axis can be vertical or horizontal.

By moving and/or pivoting the support relative to the frame, the scanner can be used for various scanning applications. With a vertical scan axis orientation, the scanner can be used to scan the head of a patient who is in the sitting or standing position. By lowering the scanner and pivoting it ninety degrees so that the scan axis is horizontal, the scanner can be used to scan the head of a patient who is lying down. In the horizontal scan axis orientation, the scanner can also be used to scan an arm or leg of the patient.

BRIEF DESCRIPTION OF THE DRAWINGS

Other advantages of the present invention can be understood by reference to the following detailed description when considered in connection with the accompanying drawings wherein.

DETAILED DESCRIPTION OF THE PREFERRED EMBODIMENTS

Figure 1:
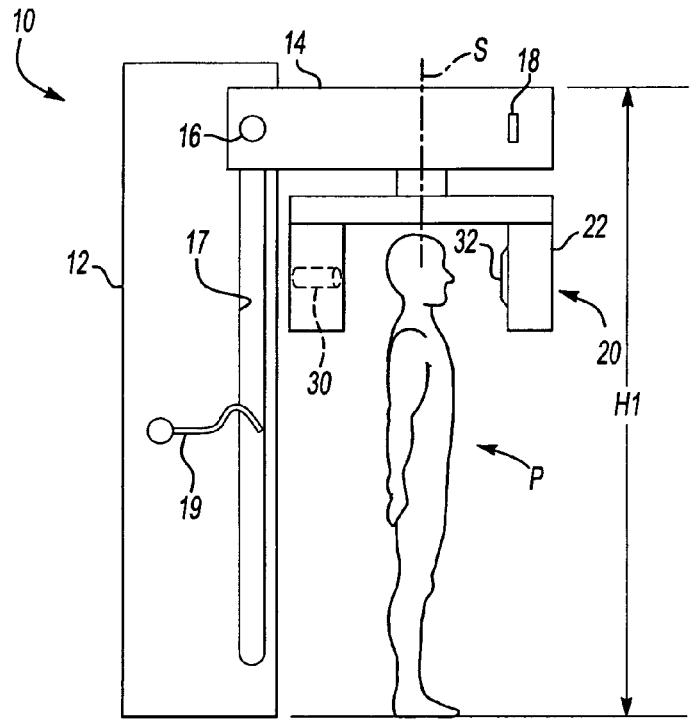
FIG. 1 is a schematic view of a CT scanner system according to a first embodiment the present invention in a vertical scan axis position.

A CT scanner system 10 according to a first embodiment of the present invention is shown schematically in FIG. 1. The system 10 includes a generally vertical frame 12 on which is mounted a support 14. A pivot axis 16 at one end of the support 14 is pivotably and slidably mounted in a track 17 in the frame 12. The support 14 includes a first latch member 18 at an opposite end of the support 14. The frame 12 includes a complementary second latch member 19 at a mid-point along the track 17.

A CT scanner 20 is mounted to the support 14. The CT scanner 20 includes a gantry 22, which rotatable about a scan axis S. In FIG. 1, the scan axis S is vertical. The CT scanner 20 generally includes an x-ray source 30 opposite an x-ray detector 32, with the scan axis S between the x-ray source 30 and x-ray detector 32.

Figure 1A:
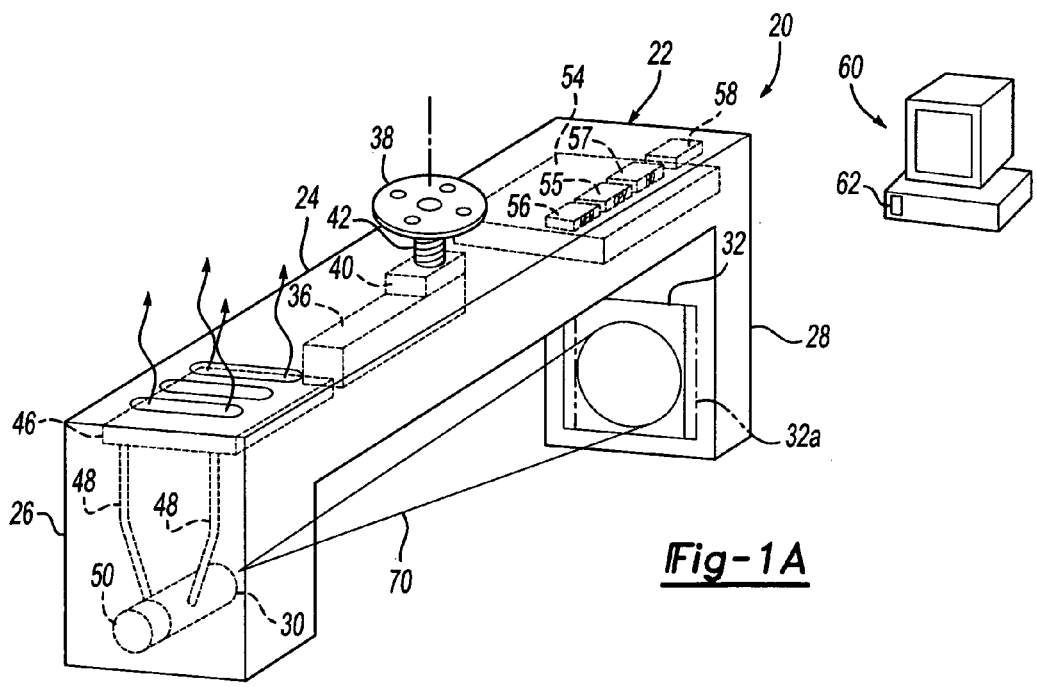
FIG. 1A is a more detailed perspective view of the CT scanner gantry of FIG. 1.

The CT scanner 20 is shown in more detail in FIG. 1A. In the CT scanner 20, all of the scanner components are contained in a gantry 22. The gantry 22 provides the structural support and the housing for the components. The gantry 22 comprises a cross-bar section 24 from which a first arm 26 and a second arm 28 extend perpendicularly from either end. The first arm 26 houses the x-ray source 30, which is preferably a cone-beam x-ray source 30, but may be a fan-beam or other x-ray source. The second arm 28 houses a complementary detector 32. The detector 32 is a two-dimensional detector as shown. The detector 32 is optionally selectively movable in a direction perpendicular to the second arm 28 and perpendicular to the axis of the x-ray beam to a position indicated in phantom as detector 32a. The detector 32 may be movable up to approximately 3 inches.

The cross-bar section 24 of the gantry 22 houses a motor 36 for rotating the gantry 22 relative to a mounting plate 38. The motor 36 may directly drive the mounting plate 38, or a gear box 40 may be provided between the motor 36 and mounting plate 38. As an additional option, a ball screw 42 may be provided between the motor 36 and mounting plate 38 for providing some translation of the gantry 22 along the axis of rotation of the motor 36. For example, the ball screw 42 would provide approximately 1 inch of translation (vertically in FIG. 1) in one complete rotation of the gantry 22.

The gantry 22 further includes a heat exchanger 46 for cooling the x-ray source 30. The heat exchanger 46 contains cooling oil circulated to and from the x-ray source 30 via lines 48. The cooling oil brings heat from the x-ray source 30 to the heat exchanger 46 for dissipation. The heat exchanger 46 may also include a fan (not shown) for cooling the cooling oil. As an alternative to or in addition to the heat exchanger 46, the CT scanner 20 may include a piezoelectric cooling system 50 (shown in phantom) for cooling the x-ray source 30.

The CT scanner 20 further includes an on-board computer 54 including a microprocessor or CPU 55, memory 56, a hard drive 57 and/or other optical, magnetic, electronic or other mass storage, and other hardware and software for performing the functions described herein. Note that for simplicity all connections between the computer 54 and the other components in the CT scanner 20 are not shown. The processor 54 in the disclosed embodiment performs at least these three functions: First, the computer 54 controls the rotation of the CT scanner 20 by controlling the motor 36. Second, the computer 54 also controls the x-ray source 30, including powering the source 30 on and off and varying the intensity of the produced x-ray. Third, the computer 54 collects the data from the detector 32 and stores it for later collection, such as in memory 56 or storage 57. If the detector 32 is movable to the position shown as detector 32a, the computer 54 also controls the movement and position of the detector 32 relative to the arm 28, via a motor or other means.

The computer 54 includes a wireless transmitter 58 for transmitting the data after collection to an off-board computer 60 that includes a complementary wireless receiver 62. The off-board computer 60 processes the data collected by the CT scanner 20 to create the 3D models and images. Optionally, the computer 54 could be connected via traditional wires or optical connections to the computer 60. Communication and power may be provided to the CT scanner 20 through wires (not shown) passing through mounting plate 38.

Optionally, the on-board computer 54 may also process the data from the detector 32, including building the 3-D model or image of what was scanned. The 3-D model would be stored in memory 56 and/or storage 57 before being transmitted to off-board computer 60.

Figure 2:
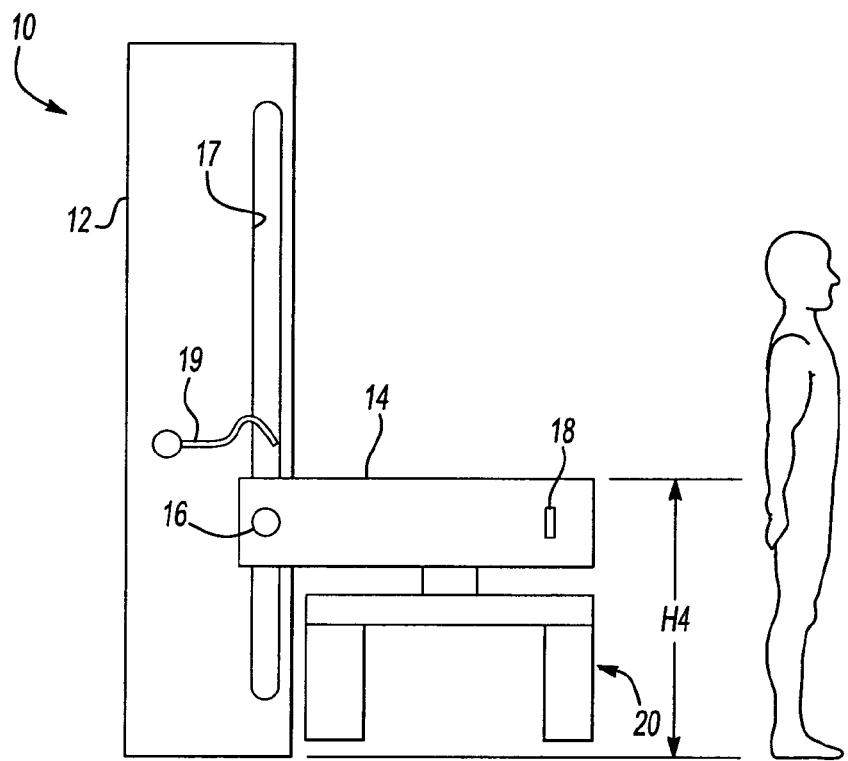
FIG. 2 shows the CT scanner system of FIG. 1 in a lower position.
Figure 3:
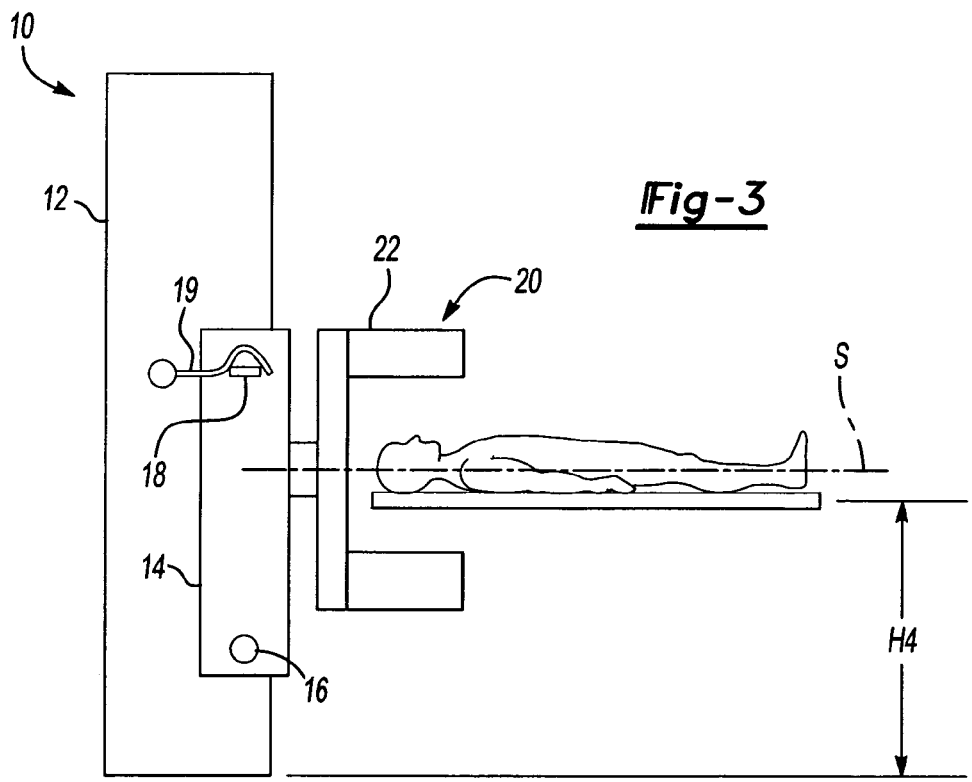
FIG. 3 shows the CT scanner system of FIG. 1 in the lower horizontal scan axis position

FIG. 2 shows the CT scanner system 10 of FIG. 1 with the CT scanner 20 in a lower position. The support 14 is moved downwardly along the track 17 until the CT scanner 20 is in the lower position. The vertical motion along the track 17 is motor-controlled. The CT scanner 20 is then pivoted about the pivot axis 16 to the horizontal scan axis orientation, as shown in FIG. 3. The first latch member 18 on the support 14 connects with the second latch member 19 on the frame 12, to hold the support 14 in the vertical orientation as shown. The CT scanner 20 scan axis S is now horizontal. In this configuration, the patient's head can be scanned while lying down on a table (as shown). Alternatively, the patient's arm or leg can be scanned while the CT scanner 20 is in the horizontal scan axis orientation.

In scanning (in the position of FIG. 1 or FIG. 2), the part of the body to be scanned is positioned between the first arm 26 and the second arm 28 of the gantry 22. The x-ray source 30 generates a cone-beam x-ray 70 that is directed toward the detector 32. The processor 54 then controls the motor 36 to perform one complete revolution of the gantry 22 about the scan axis S, during which time the computer 54 collects multiple images from the detector 32. The images taken by detector 32 are stored in memory 56 and/or storage 57. The data collected by the computer 54 is then transmitted via transmitter 58 to the receiver 62 and collected by the computer 60. The computer 60 then generates the 3-D models or images of the scanned body part based upon the data. The images are stored on-board the CT scanner 20 at least temporarily and then transmitted to the off-board computer 60.

Figure 4:
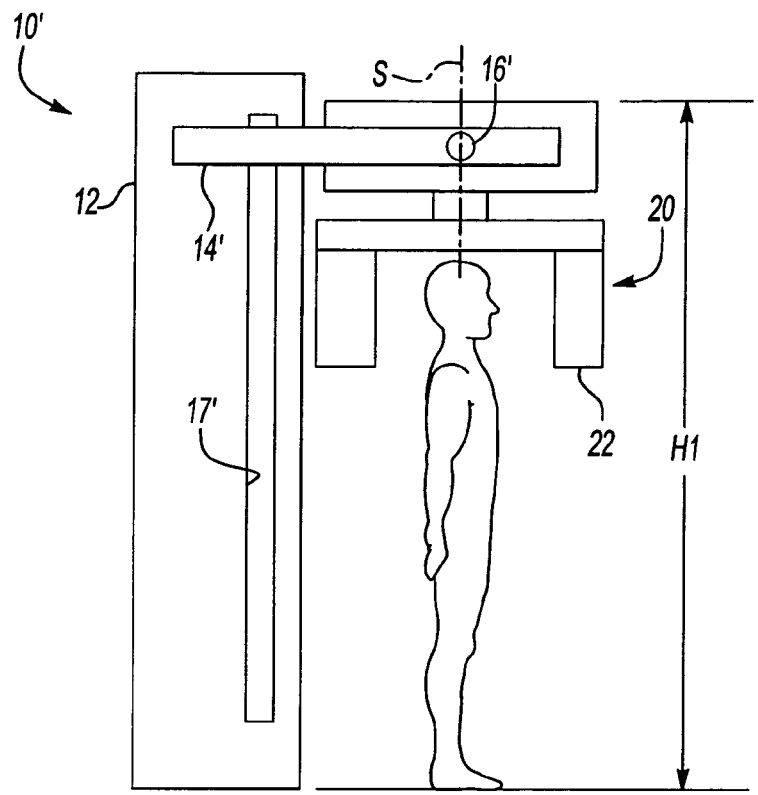
FIG. 4 is a schematic view of a CT scanner system according to a second embodiment the present invention in a vertical scan axis position.

FIG. 4 is a schematic view of a CT scanner system 10' according to a second embodiment the present invention in a vertical scan axis position. In this second embodiment, identical components are given the same reference numerals as the first embodiment, while corresponding, similar components are given reference numerals with a prime designation. In the CT scanner system 10', the support 14' is slidably (but not pivotably) mounted on the track 17' on the frame 12. The gantry 22 of the CT scanner 20 is pivotably mounted to the support 14' at a pivot axis 16'. The pivoting connection would include detents and/or other ways or other manual locking devices (such as pegs) for locking the gantry 22 into a desired position relative to the support 14'.

Figure 4A:
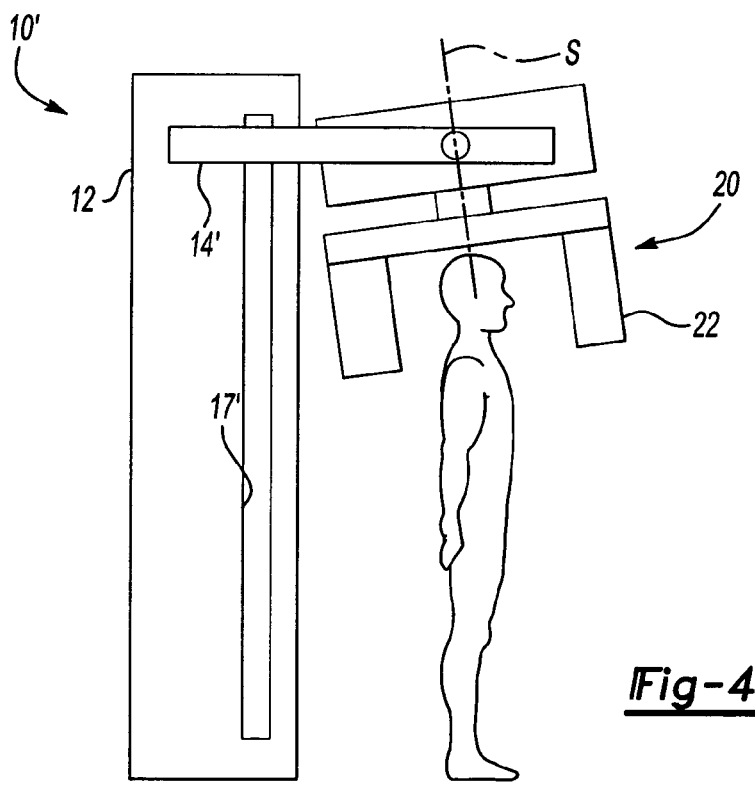
FIG. 4A shows the CT scanner system of FIG. 4 in a slightly tilted scan axis position.

The gantry 22 can preferably be rotated to any position between a vertical scan axis S, as shown in FIG. 4, to a horizontal scan axis. For example, as shown in FIG. 4A, the CT scanner 20 can be pivoted slightly so that the scan axis S is ten degrees (for example) relative to vertical.

Figure 5:
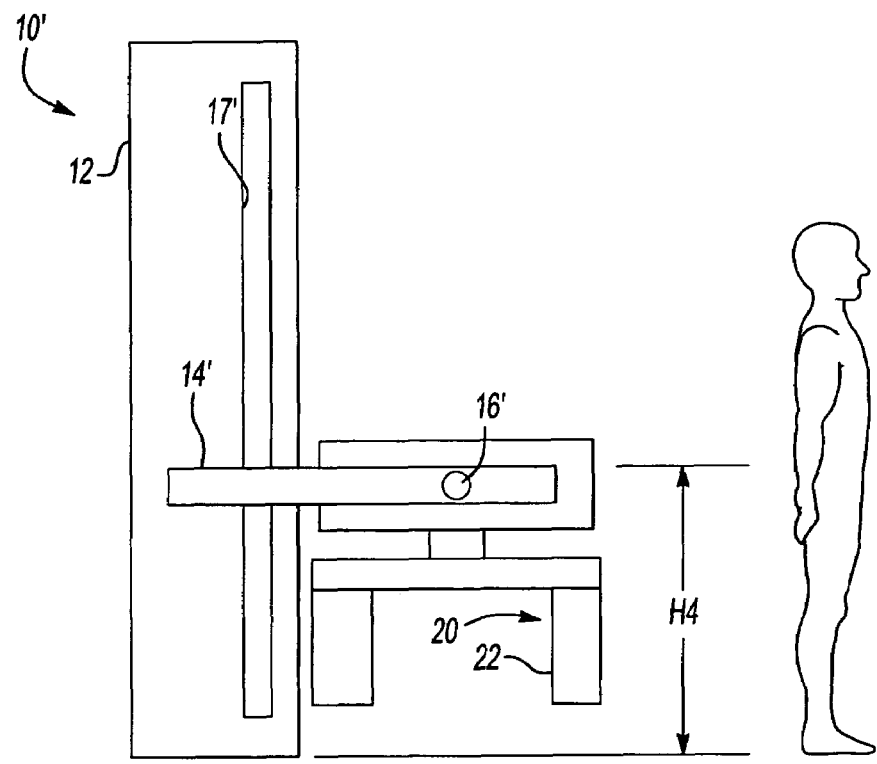
FIG. 5 shows the CT scanner system of FIG. 4 in a lower position.
Figure 6:
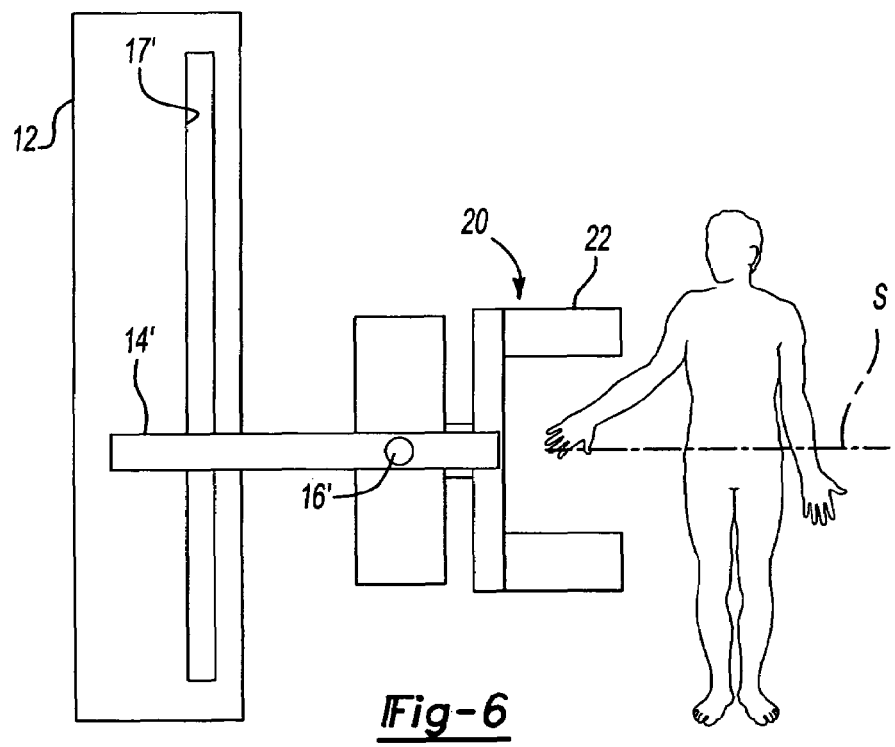
FIG. 6 shows the CT scanner system of FIG. 4 in the lower horizontal scan axis position

FIG. 5 shows the CT scanner system 10' with the CT scanner 20 moved to the lower position (e.g. via motor control). The gantry 22 is then pivoted about the pivot axis 16' ninety degrees to the orientation shown in FIG. 6, where the scan axis S is in the horizontal orientation. In this configuration, the CT scanner 20 can be used to scan an arm or a leg of the patient.

Figure 7:
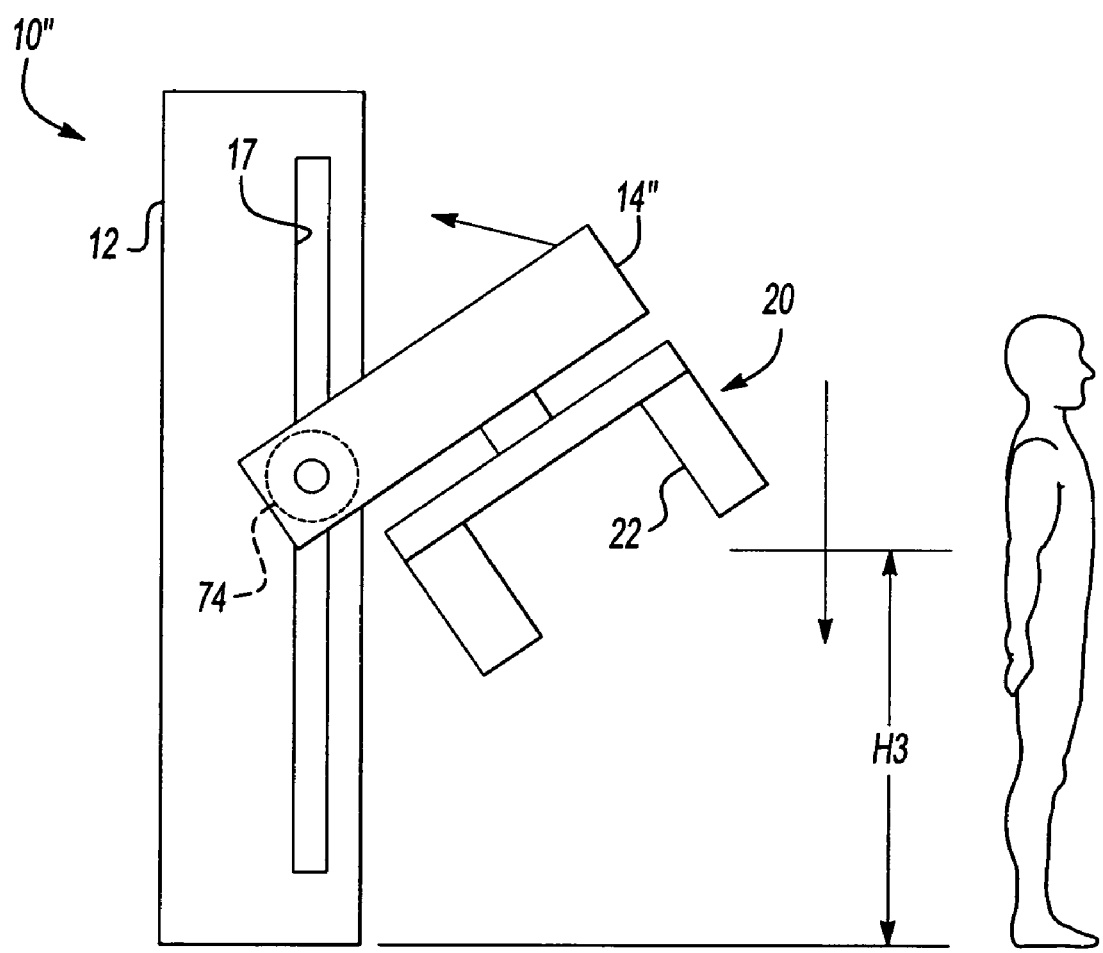
FIG. 7 is a schematic view of a CT scanner system according to a third embodiment the present invention.

FIG. 7 is a schematic view of a CT scanner system 10" according to a third embodiment the present invention. Components corresponding to those in the second embodiment are indicated with a double prime designation. In the third embodiment, the components and operation are generally the same as that of the first, with the addition of a motor 74 mounted with the support 14" for controllably pivoting the support 14" relative to the frame 12. Alternatively, the motor 74 could be mounted in the frame 12. The motor 74 pivots the support 14" ninety degrees (in any increment) from a horizontal scan axis orientation to a vertical scan axis orientation. The support 14" is also movable (via motor control) vertically relative to the frame 12, as in previous embodiments. Preferably, the operator can lower the support 14" via a motor control. As the operator keeps lowering the support 14" below a certain height, the motor 74 starts tilting the support 14" to the horizontal scan axis orientation.

In combination with any one of the above embodiments, the shaft of the support 14, 14', 14" can be made wider so that a patient's leg can fit through it.

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope. Alphanumeric labels on method steps are for ease of reference in dependent claims and unless otherwise specified do not require a specific sequence in which the steps are to be performed.

What is claimed is:

1. A reconfigurable CT scanner comprising:

a frame;

a support mounted to the frame, the support pivotable about a pivot axis relative to the frame;

a gantry mounted to the support, the gantry rotatable about a scan axis relative to the support and rotatably connected to the support at the scan axis, the scan axis orthogonal to the pivot axis, the pivot axis spaced away from the scan axis, such that rotation of the gantry about the pivot axis rotates the scan axis between a position generally parallel to a floor to a position generally transverse to the floor;

an x-ray source mounted to the gantry;

an x-ray detector mounted to the gantry opposite the x-ray source, the scan axis between the x-ray source and the x-ray detector; and a computer programmed to create a CT image based upon a plurality of images received from the x-ray detector at a plurality of rotational positions.

2. The reconfigurable CT scanner of claim 1 wherein the support is pivotable approximately ninety degrees about the pivot axis.

3. The reconfigurable CT scanner of claim 2 wherein the pivot axis is transverse to the scan axis.

4. The reconfigurable CT scanner of claim 1 wherein the support is slidable relative to the frame.

5. The reconfigurable CT scanner of claim 4 wherein the support is slidable vertically relative to the frame.

6. The reconfigurable CT scanner of claim 1 wherein the support is pivotable approximately ninety degrees about the pivot axis between a first position and a second position, and the gantry is rotatable about the scan axis when the support is in the first position and when the support is in the second position.

7. The reconfigurable CT scanner of claim 1 wherein the x-ray source is a cone-beam x-ray source.

8. The reconfigurable CT scanner of claim 1 wherein the support is pivotably connected to the frame at one end of the support.

9. The reconfigurable CT scanner of claim 1 wherein the support is pivotable between a first position generally parallel to a floor and a second position generally perpendicular to a floor.

10. A reconfigurable CT scanner comprising:

a frame;

a gantry including a cross section, and a first arm and a second arm extending from the cross section, the gantry mounted to the frame, the gantry slidable vertically relative to the frame and pivotable about a pivot axis relative to the frame, the gantry rotatable about a scan axis extending through the cross section, the scan axis spaced away from the pivot axis, such that rotation of the gantry about the pivot axis rotates the scan axis between a position generally parallel to a floor to a position generally transverse to the floor;

an x-ray source mounted to the first arm;

an x-ray detector mounted to the second arm opposite the x-ray source, the scan axis between the x-ray source and the x-ray detector; and a computer programmed to create a CT image based upon a plurality of images received from the x-ray detector at a plurality of rotational positions about the scan axis.

11. The reconfigurable CT scanner of claim 10 wherein the pivot axis is orthogonal to the scan axis.

12. The reconfigurable CT scanner of claim 10 wherein the pivot axis is not parallel to the scan axis.

13. The reconfigurable CT scanner of claim 10 further including a support mounted to the frame, the support pivotable about a pivot axis relative to the frame, the gantry rotatably mounted to the support to rotate about the scan axis.

* * * * *